United States Patent
Deck et al.

(10) Patent No.: US 10,537,357 B2
(45) Date of Patent: Jan. 21, 2020

(54) INSERTION DEVICE

(71) Applicant: ROCHE DIABETES CARE, INC., Indianapolis, IN (US)

(72) Inventors: Frank Deck, Niederkirchen (DE); Christian Hoerauf, Oftersheim (DE); Michael Keil, Ludwigshafen (DE); Ahmet Konya, Ludwigshafen (DE); Thomas Weiss, Mannheim (DE); Oliver Kube, Worms (DE); Karl-Peter Ebert, Fraenkisch-Crumbach (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 169 days.

(21) Appl. No.: 15/434,412

(22) Filed: Feb. 16, 2017

(65) Prior Publication Data

US 2017/0156753 A1  Jun. 8, 2017

Related U.S. Application Data

(63) Continuation of application No. 13/079,957, filed on Apr. 5, 2011, now Pat. No. 9,629,958, which is a
(Continued)

(30) Foreign Application Priority Data

Oct. 7, 2008 (EP) .................... 08017529

(51) Int. Cl.
*A61B 17/34* (2006.01)
*A61B 5/145* (2006.01)
(Continued)

(52) U.S. Cl.
CPC ...... *A61B 17/3403* (2013.01); *A61B 5/14503* (2013.01); *A61B 5/14532* (2013.01);
(Continued)

(58) Field of Classification Search
CPC ........ A61B 17/2909; A61B 2017/2912; A61B 2017/2923; A61B 5/1411; A61B 5/151;
(Continued)

(56) References Cited

U.S. PATENT DOCUMENTS 4,448,193 A   5/1984  Ivanov
5,527,334 A * 6/1996  Kanner .............. A61B 5/15142
                                                    600/583
(Continued)

FOREIGN PATENT DOCUMENTS

CN    2094999 U   2/1992
CN    2772443 Y   4/2006
(Continued)

OTHER PUBLICATIONS

English Translation of International Search Report, PCT/EP2009/006823, dated Aug. 2, 2010, 2 pages.
(Continued)

*Primary Examiner* — Diane D Yabut
(74) *Attorney, Agent, or Firm* — Bose McKinney & Evans LLP (57) ABSTRACT

An insertion device including an insertion needle holder and a drive mechanism for linearly moving the insertion needle holder in a puncturing direction. The insertion needle holder also includes at least one actuating element for actuating a drive mechanism. The drive mechanism converts a driving motion of the actuating element, which extends transversely or opposite to the puncturing direction, into a puncturing motion of the insertion needle holder.

14 Claims, 6 Drawing Sheets

Related U.S. Application Data continuation of application No. PCT/EP2009/006823, filed on Sep. 22, 2009.

(51) Int. Cl.
  *A61M 5/158* (2006.01)
  *A61B 90/11* (2016.01)
  *A61B 5/00* (2006.01)
  *A61B 17/29* (2006.01)
  *A61B 17/00* (2006.01)

(52) U.S. Cl.
  CPC ........ *A61B 5/6846* (2013.01); *A61B 17/3415* (2013.01); *A61B 17/3468* (2013.01); *A61B 90/11* (2016.02); *A61M 5/158* (2013.01); *A61B 17/2909* (2013.01); *A61B 2017/00407* (2013.01); *A61B 2017/2912* (2013.01); *A61B 2017/2923* (2013.01); *A61B 2017/3409* (2013.01); *A61M 2005/1585* (2013.01)

(58) Field of Classification Search
  CPC ............ A61B 5/157; A61M 2005/1585; F16H 19/02; F16H 19/04; F16H 19/043; F16H 2019/046
  See application file for complete search history.

(56) References Cited

U.S. PATENT DOCUMENTS

| | | |
|---|---|---|
| 5,938,679 A | 8/1999 | Freeman et al. |
| 7,052,483 B2 | 5/2006 | Wojcik |
| 7,310,544 B2 | 12/2007 | Brister et al. |
| 2001/0056286 A1* | 12/2001 | Etter .................. A61B 17/2909 606/205 |
| 2002/0077599 A1 | 6/2002 | Wojcik |
| 2002/0123740 A1 | 9/2002 | Flaherty et al. |
| 2005/0245956 A1 | 11/2005 | Steinemann et al. |
| 2006/0020189 A1 | 1/2006 | Brister et al. |
| 2006/0135908 A1 | 6/2006 | Liniger et al. |
| 2006/0155317 A1 | 7/2006 | List |
| 2006/0173410 A1 | 8/2006 | Moberg et al. |
| 2006/0183984 A1 | 8/2006 | Dobbles et al. |
| 2008/0004512 A1 | 1/2008 | Funderburk et al. |
| 2008/0009805 A1 | 1/2008 | Ethelfeld |
| 2008/0051714 A1 | 2/2008 | Moberg et al. |
| 2008/0208139 A1 | 8/2008 | Scheurer et al. |
| 2008/0275407 A1 | 11/2008 | Scheurer |
| 2011/0106126 A1 | 5/2011 | Love et al. |

FOREIGN PATENT DOCUMENTS

| | | |
|---|---|---|
| EP | 1764122 A1 | 3/2007 |
| EP | 1829578 A2 | 9/2007 |
| WO | WO 03070303 A2 | 8/2003 |
| WO | WO 2004/098684 A2 | 11/2004 |

OTHER PUBLICATIONS

English Translation of Written Opinion of the International Searching Authority, PCT/EP2009/006823, dated Aug. 2, 2010, 5 pages.
English Translation of International Preliminary Report on Patentability, PCT/EP2009/006823, dated Apr. 12, 2011, 6 pages.

* cited by examiner

INSERTION DEVICE

RELATED APPLICATIONS

This application is a continuation of U.S. patent application Ser. No. 13/079,957, filed Apr. 5, 2011, now U.S. Pat. No. 9,629,958, which is a continuation of International Application No. PCT/EP2009/006823 filed Sep. 22, 2009, which claims priority to EP Application No. 08017529.2 filed Oct. 7, 2008. Each of the referenced applications is incorporated herein by reference in its entirety.

TECHNICAL FIELD OF THE INVENTION

The invention relates to an insertion device for insertion of an article into a human body.

BACKGROUND

Insertion devices that induce a puncturing motion of an insertion needle using a drive mechanism are used to insert sensors for measuring analyte concentrations, for example glucose concentrations, in vivo in a patient's bodily tissue, such as in subcutaneous fatty tissue. Insertion needles commonly used for this purpose are designed as hollow needles or V-shaped grooves in which a sensor is disposed. The sensor can be designed, for example, as an electrode system for electrochemical measurements, or can comprise a microfluidic catheter for the inflow and outflow of perfusion fluid. After a puncture is made, the insertion needle is withdrawn from the bodily tissue and the sensor remains in the puncture site.

Insertion devices are also used, for example, to apply catheters such as for the infusion of insulin or other active agents.

In the case of simple insertion devices, a drive mechanism converts a driving motion of an actuating element into a linear puncturing motion of the insertion needle. The force required to make a puncture must be applied by the user himself using a driving motion of the actuating element during the insertion procedure. As such, many users are reluctant to use such insertion devices on themselves in order to, for example, insert a sensor into the subcutaneous fatty tissue of the abdomen. In particular, persons who have limited range of motion due to age or illness find it difficult to hold an insertion device against their body at the correct angle and apply the proper amount of force required to make a puncture. The action of applying force makes it difficult to hold the insertion device steady and prevent it from tilting during actuation. If the person's hand shakes during puncturing, or if the insertion device tilts, the insertion needle undergoes transverse motions which are painful; in the extreme case, the insertion attempt fails. In particular, transverse motions that occur during puncturing can result in the inserted sensor being ultimately exposed to mechanical stresses from surrounding bodily tissue, which can apply loads upon the sensor and even bend it. In addition, the bodily tissue is constantly irritated, thereby resulting in a greater incidence of inflammation and rejection responses, all of which negatively affect the sensor measurements.

These disadvantages can be largely eliminated by using more complex insertion devices having spring-driven drive mechanisms. In the case of such insertion devices, the energy required for the puncturing motion is delivered by a drive spring or another energy accumulator. For insertion, a user merely needs to place such an insertion device on a suitable point on the body and trigger a puncture by pressing a release element. The amount of force required therefore is minimal, and so even persons who have limited mobility can easily hold the insertion device steady during the insertion procedure.

SUMMARY

The invention provides an easy-to-use insertion device comprising an insertion needle holder and a drive mechanism for linearly moving the insertion needle holder in a puncturing direction. The insertion needle holder also includes at least one actuating element for actuating a drive mechanism. The drive mechanism converts a driving motion of the actuating element, which extends transversely or opposite to the puncturing direction, into a puncturing motion of the insertion needle holder.

In the insertion devices disclosed herein, although a user applies the force required for a puncturing motion by manually operating the actuating element, the insertion devices are very easy to handle since the driving motion of the actuating element extends transversely to the insertion direction. A motion extending transversely to the puncturing direction is much easier to perform than a motion in the puncturing direction, for ergonomic reasons. The same applies for a motion opposite to the puncturing direction. Thus, even persons who have limited mobility can insert a sensor, infusion catheter, or other article, for example, into the upper arm or the subcutaneous fatty tissue of the abdomen or other suitable location, using a steady hand and the insertion devices disclosed herein.

In addition, since with the insertion devices disclosed herein the force required to perform the puncturing motion is applied transversely or opposite to the puncturing direction, a user does not have the feeling that he is applying this force to himself. Even if the puncturing motion takes place during the driving motion, a small psychological barrier must still be overcome to actuate the insertion device. In contrast, the reservation that any person would have, to a greater or lesser extent, about intentionally propelling a sharp object toward his own body with strong force is not an issue with the insertion devices described herein. Also, since the driving motion of the actuating element is transverse to the puncturing direction, the insertion device itself—and not person's body—functions as the abutment of the actuating force. This makes it easier for a user to relax the body part into which he intends to inject the insertion needle and to more steadily hold the insertion device, thereby reducing the pain of insertion and the mechanical stresses involved.

In one embodiment, the insertion device can be designed such that the driving motion of the actuating element that extends transversely to the puncturing direction occurs perpendicularly to the puncturing direction. This is not required, however. A driving motion that occurs in another direction that is not parallel to the puncturing direction also extends transversely to the puncturing direction is also contemplated. In particular, it is not required for the driving motion of the actuating element to be a linear motion. For example, the driving motion of the actuating element can also be a swivelling motion. The smaller the angle is that is traversed in a swivelling motion, and the greater the radius of the swivelling motion is, the lesser the difference is from a linear motion, from an ergonomic perspective.

The insertion devices described herein do not require a spring or any other energy accumulator. The drive mechanism of the insertion devices can therefore be constructed without an energy accumulator, thereby making it cost-favorable. Thus, the insertion devices can also be designed as a disposable article that is discarded after a single use. A safeguard against unwanted re-use can be implemented by designing the drive mechanism to become locked after use. For example, actuating element can be designed to snap into position at the end of the driving motion.

If a particularly rapid puncturing motion of the insertion needle is desired, this can be realized by using the operator's hand as an energy accumulator. One possibility in this regard is to block motion of the actuating element using a locking element that is not overcome until a specified force is reached. For example, a locking element can be designed to break or be overcome via elastic deformation. Since such a locking element is overcome suddenly, the user moves the actuating element substantially more rapidly than would be possible otherwise without such a locking element.

The insertion devices described herein can also be designed to be reused by allowing new insertion needles to be inserted into the insertion needle holder at any time. In the case of a disposable device for single use, although an insertion needle has typically already been inserted into the insertion needle holder by the manufacturer, insertion devices for multiple use that do not have insertion needles installed in the insertion needle holder can also be marketed and sold, since a user can insert insertion needles that are sold separately into the insertion needle holder. In the case of a reusable insertion device, it can be provided with a return spring that moves the actuating element(s), once they have been actuated, back to a starting position for reuse. The mechanical requirements on such a return spring are extraordinarily low, thereby ensuring that such a return spring can be manufactured cost-favorably, such as by being made from plastic.

In one embodiment of the insertion devices, a drive mechanism comprising a connecting rod can be used to convert the driving motion of the actuating element, which extends transversely to the puncturing direction, into a linear puncturing motion of the insertion needle holder. Since the driving motion initially induces rotary motion or a swivelling motion, the linear motion required for a puncturing motion can be easily generated in this manner. Instead of a connecting rod, a four-bar mechanism can be used, for instance. The drive mechanism can also include a rotor coupled to the actuating element, and a connecting rod that is coupled to the rotor and can convert rotary motion of the rotor into a linear motion of the insertion needle holder. The actuating element can be coupled to the rotor by, for example, a rack.

In the case of the insertion devices described herein, it is basically sufficient to provide a single actuating element which can be moved transversely to the puncturing direction. However, it is also possible to equip the insertion devices with two diametrically opposed actuating elements. Transverse forces and reaction forces exerted by the actuating elements on the device or the drive mechanism can be compensated for in this manner. In addition, a device that comprises two diametrically opposed actuating elements can be used equally easily by right-handed persons and left-handed persons. The two actuating elements can be coupled to the drive mechanism in a manner such that they move in opposite directions when a puncturing motion occurs. For example, the two actuating elements can move toward one another when an insertion motion occurs. This makes it possible to apply the force required for a puncturing motion manually, for example, in that the device is grasped with one hand and then squeezed using the hand. Making such a motion is similar to forming a fist and is therefore a very simple motion that does not require a particular level of precision or coordination. Motions of that type can also be carried out without a reaction force being transferred to the patient's body. The risk of the device tilting during the insertion procedure is therefore substantially reduced.

Insertable sensors can be used together with a sensor holder which can be taped to a patient's abdomen. To insert a sensor, an insertion device can be coupled to such a sensor holder. Once insertion has been completed, the insertion device is typically released from the sensor holder which remains on the patient's body. Adhesive sensor holders and an inserter therefore are known e.g. from US 2006/0183984 A1, which is incorporated herein by reference.

Thus, according to another aspect of the invention, the insertion device comprises a coupling mechanism that, for insertion, holds a sensor holder against an insertion device and is actuated by the drive mechanism at the end of an insertion procedure to detach the sensor holder from the insertion device. In addition to this automatic decoupling which occurs once insertion has been completed, premature decoupling can be enabled, for example, to halt a painful insertion. For this purpose, the coupling mechanism can be provided with an actuating element which a user can actuate without affecting the drive mechanism. In one embodiment, the coupling mechanism comprises two arms which are hingedly interconnected, hold the sensor holder, and are moved by the drive mechanism to decouple the insertion device from the sensor carrying device.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following description. Rather, the embodiments are chosen and described so that others skilled in the art may appreciate and understand the principles and practices of this disclosure.

Figure 1:
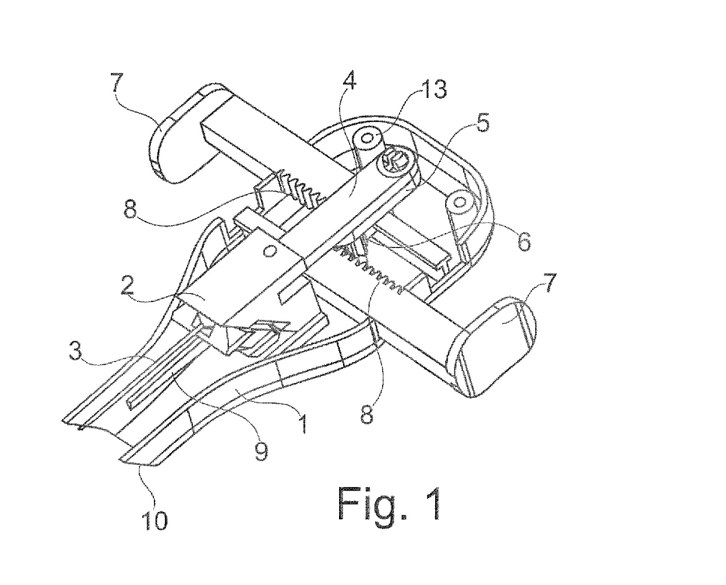
FIG. 1 shows an embodiment of an insertion device according to the invention, with the housing opened.

The insertion device depicted in FIG. 1 has a housing 1, in which an insertion needle holder 2 can move linearly in a puncturing direction. The insertion needle holder with an insertion needle 3 installed is shown in FIG. 1. Insertion needle holder 2 is coupled to a drive mechanism which, in the embodiment shown, comprises a connecting rod 4, a crank 5, a rotor 6 designed as a toothed wheel, and two actuating elements 7. Actuating elements 7 are provided with racks 8 which mesh with rotor 6 designed as a toothed wheel. When the two actuating elements 7 are pressed into housing 1, i.e. are moved toward one another perpendicularly to the puncturing direction, rotor 6 designed as a toothed wheel is set into rotary motion. Rotor 6 is coupled via a crank 5 to connecting rod 4 which converts the rotary motion of rotor 6 into linear motion of insertion needle holder 2. As a result, the puncturing motion of insertion needle 3 occurs during the driving motion of actuating elements 7.

In the starting state depicted in FIG. 1, the two actuating elements 7 extend laterally out of housing 1 of the insertion device. In the case of a single-use device in particular, which is required to be discarded after a single use, actuating elements 7 which extend laterally out of the housing can be provided with an originality safeguard e.g. a sealing film, to show the user that the device is new. Once the originality safeguard has been removed, the insertion device can be grasped by the hand, the widened housing end coming to rest in the ball of the hand, and the two actuating elements 7 being enclosed by the thumb and the index finger. When the user then presses the two actuating elements 7 toward one another, they undergo a driving motion that extends transversely to the puncturing direction and is converted by the above-described driving mechanism into a linear puncturing motion of insertion needle holder 2. A linear guide 9 is provided to minimize painful transverse motions of insertion needle 3. Insertion needle holder 2 is coupled to linear guide 9 which can be a rail, for example, on or along which insertion needle holder 2 glides. Transverse forces exerted by actuating elements 7 on rotor 6 cancel each other out, thereby preventing the rotor from undergoing evasive maneuvers which increase friction.

Housing 1 comprises an underside 10 which extends obliquely to the puncturing direction, and is used to place the insertion device against a patient's body for use. In one embodiment, underside 10 extends at an angle of 30° to 60° relative to the puncturing direction, thereby enabling an insertion needle 3 to be inserted obliquely into the subcutaneous fatty tissue of a user. A user cannot see insertion needle 3 through housing 1, which is advantageous for psychological reasons.

The insertion device shown is used to insert a sensor for in vivo measurements, such as to measure glucose concentration. The drive mechanism therefore converts the driving motion of actuating elements 7, which extends transversely to the puncturing direction, into puncturing motion and, immediately thereafter, into retraction motion of insertion needle holder 2. This is achieved in that the lengths of racks 8 of actuating elements 7 are designed to implement exactly one full 360° revolution of rotor 6. At the anterior inflection point of the motion of insertion needle holder 2, a sensor that is coupled to insertion needle 3 is separated from insertion needle 3 and thus remains in the patient's body, in the puncture site, when the retraction motion occurs. A sensor is inserted in this manner in the continuous sequence of motion. The patient only perceives a starting state when the insertion device is placed in position, and an end state once insertion has been completed.

Once the actuating travel has been completed, actuating elements 7 engage, for example, by snapping into or together with housing 1. The drive mechanism thereby becomes locked, ensuring that the insertion device can be used only for a single use. Moreover, the locking of the drive mechanism ensures that insertion needle 3 remains in housing 1 after use, thereby protecting the user against injury by a used insertion needle 3.

In the case of the insertion device shown, the force required for a puncturing motion when the user performs the puncture is generated by the manual operation of actuating elements 7. Therefore neither a drive spring nor any other energy accumulator is required. The insertion device shown therefore does not have an energy accumulator. Insertion devices that do not have an energy accumulator are also referred to as manual insertion devices.

Figure 2:
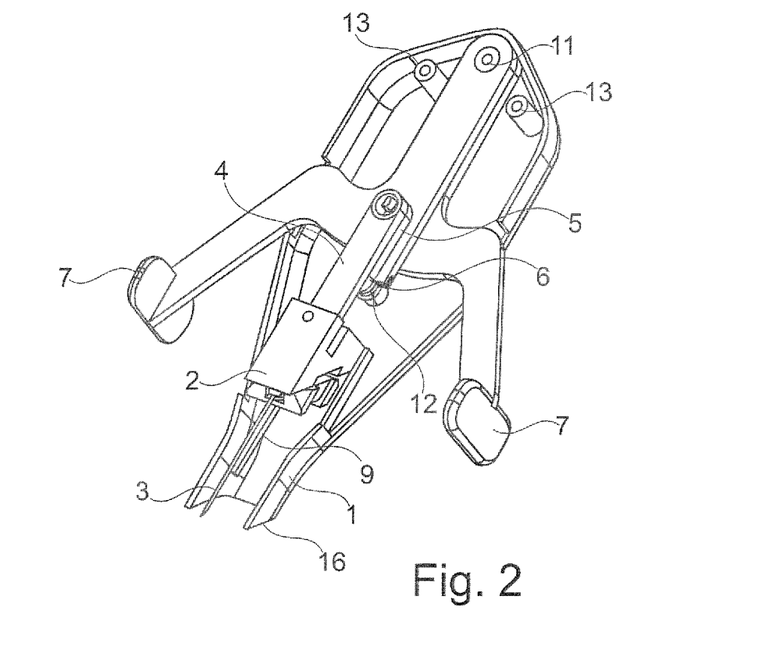
FIG. 2 shows a further embodiment of an insertion device according to the invention, with the housing opened.

FIG. 2 shows a further embodiment of an insertion device that differs from the above-described embodiment only in terms of the design of the drive mechanism. While the drive motion of actuating elements 7, which extends transversely to the puncturing direction, is a linear motion in the embodiment described above, actuating elements 7 in the embodiment depicted in FIG. 2 perform a swivelling motion. For this purpose, actuating elements 7 are pivotably supported in housing 1 using a rocker pivot 11, for example, on a pivot bolt 11.

To actuate the drive mechanism, the two actuating elements 7 are pressed together just as they are in the above-described embodiment. Actuating elements 7 are coupled via a filament 12 to a rotor 6 designed as a crankshaft, and therefore the swivelling motion of actuating elements 7 causes rotor 6 to undergo rotary motion. As in the above-described embodiment, rotor 6 is coupled via a crank 5 to connecting rod 4, and therefore the rotary motion of rotor 6 is converted into a linear puncturing motion of insertion needle holder 2.

Figure 3:
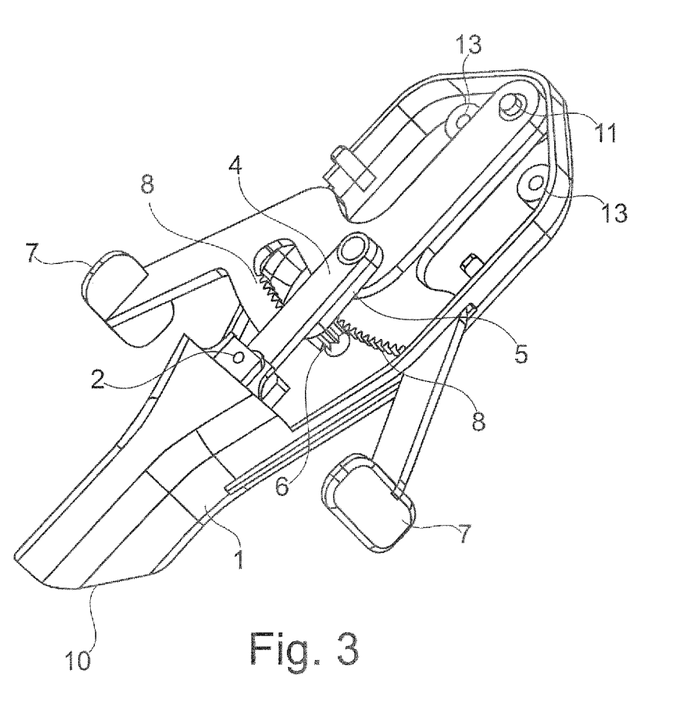
FIG. 3 shows a further embodiment of an insertion device according to the invention, with the housing opened.

FIG. 3 shows a modification of the embodiment depicted in FIG. 2. In this embodiment, the two actuating elements 7 undergo swivelling motion, just as in the embodiment depicted in FIG. 2. Similar to the embodiment depicted in FIG. 1, however, actuating elements 7 are provided with racks 8 which mesh with rotor 6 designed as a toothed wheel. In this embodiment as well, the swivelling motion of actuating elements 7 about pivot bolt 11 therefore induces rotary motion of rotor 6 via curved racks 8, the linear motion being converted via a connecting rod 4 into linear motion of insertion needle holder 2.

Housings 1 of the insertion devices can be formed e.g. by joining two half shells. For this purpose, one of these half shells can be provided with pivot bolts or other connecting elements which engage in complementary connecting elements 13 of the other half shell e.g. in hollow studs or sockets. It is also possible to design the housing to be single-pieced, as two halves that are connected via a film hinge and are folded together to close the housing and snap into position or are connected in a bonded manner e.g. by adhesion or welding. A film hinge is a connection between two components that is flexible due to its reduced material thickness and thereby enables the two components to swivel relative to one another.

To reduce the number of components required, such a film hinge can also be used at other points in the embodiments described. For example, insertion needle holder 2 can be joined via a film hinge to connecting rod 4. It is also possible to replace rocker pivot 11 in the embodiment shown in FIG. 2 with a film hinge.

Figure 4:
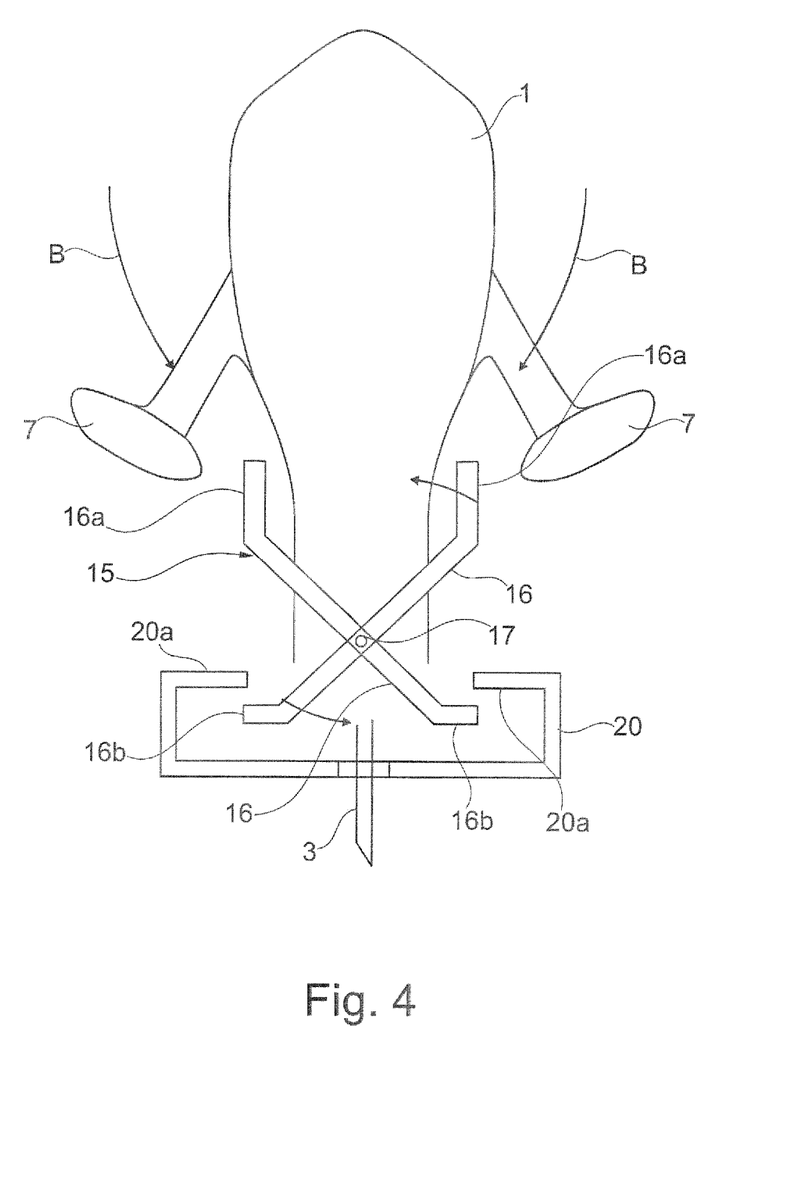
FIG. 4 shows a schematic depiction of the coupling of an insertion device to a sensor holder.

FIG. 4 shows, in a schematic depiction, an embodiment of a sensor holder 20 which is coupled together with an insertion device of the type described above, for example with reference to FIG. 2 or 3, and which can be taped to a patient's abdomen for insertion of a sensor.

In the embodiment depicted in FIG. 4, the insertion device comprises a coupling mechanism 15, via which the insertion device is coupled to sensor holder 20 for insertion. Coupling mechanism 15, which is depicted schematically, is designed as articulated levers. Two lever arms 16 are situated such that they cross over one another and can swivel about a connection point 17. In the coupling position depicted in FIG. 4, lower ends 16b of lever arms 16 extend behind holding elements 20a of sensor holder 20 and thereby establish a mechanical connection between the insertion device and sensor holder 20.

To perform insertion, the two actuating elements 7 of the insertion device are moved along a curve as indicated by arrow B in FIG. 4, as explained above with reference to FIGS. 2 and 3. When this motion comes to an end, actuating elements 7 impact upper ends 16a of lever arms 16 of coupling mechanism 15. As a result, upper ends 16a of lever arms 16 are pressed together, thereby moving lower ends 16b thereof toward one another and disengaging them from sensor holder 20. In this manner, the insertion device shown automatically decouples from sensor holder 20 at the end of an insertion procedure and can be easily removed therefrom. Upper ends 16a of lever arms 16 thus form actuating elements of the coupling mechanism.

A user may also detach the insertion device from the sensor holder by pressing with his fingers on upper ends 16a of lever arms 16 and thereby operate the articulated lever mechanism. In this manner a user is able to abort an insertion procedure and remove the insertion device from the sensor holder.

Figure 5:
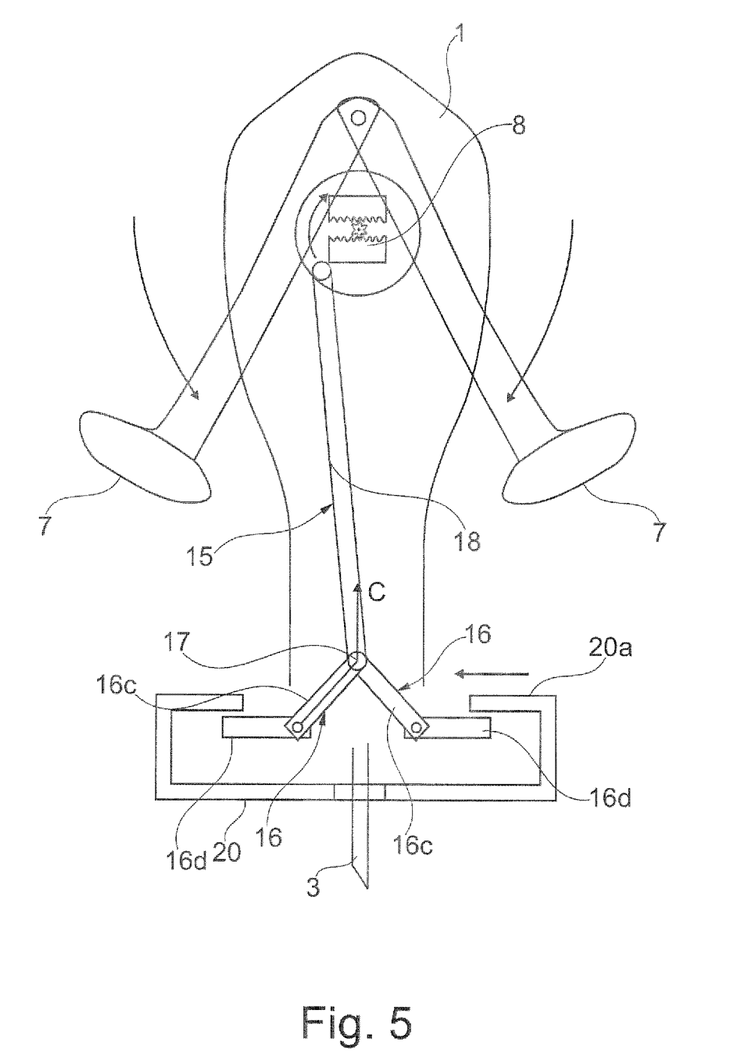
FIG. 5 shows a schematic depiction of a further embodiment of the coupling of an insertion device to a sensor holder.

FIG. 5 shows a schematic depiction of a further embodiment of a coupling mechanism 15 which connects the insertion device to a sensor holder 20 for insertion, and decouples therefrom once insertion has been completed.

Coupling mechanism 15, which is depicted schematically in FIG. 5, has two arms 16 which are hingedly connected to one another at a connecting point 17. Each arm 16 includes an upper arm 16c and a lower arm 16d which are hingedly connected to one another in the manner of an elbow. In the coupling position depicted in FIG. 5, lower arms 16d engage in holding elements 20a of sensor holder 20 and thereby establish a mechanical connection between the insertion device and sensor holder 20.

At the end of an insertion procedure, coupling mechanism 15 is actuated, similar to the above-described embodiment, by the drive mechanism of the insertion device, and therefore the two joint arms 16 of coupling mechanism 15 are retracted at connection point 17 thereof in the direction of arrow C. Lower arms 16d thereby move toward one another and disengage coupling mechanism 15 from sensor unit 20.

In the embodiment depicted in FIG. 5, coupling mechanism 15 comprises a sinusoidal link mechanism having an arm 18 which is hingedly connected, as a connecting rod, to connection point 17 of the two arms 16. The sinusoidal link mechanism is driven via racks 8 of the drive mechanism, thereby decoupling sensor holder 20 from the insertion device at the end of an insertion procedure.

Figure 6:
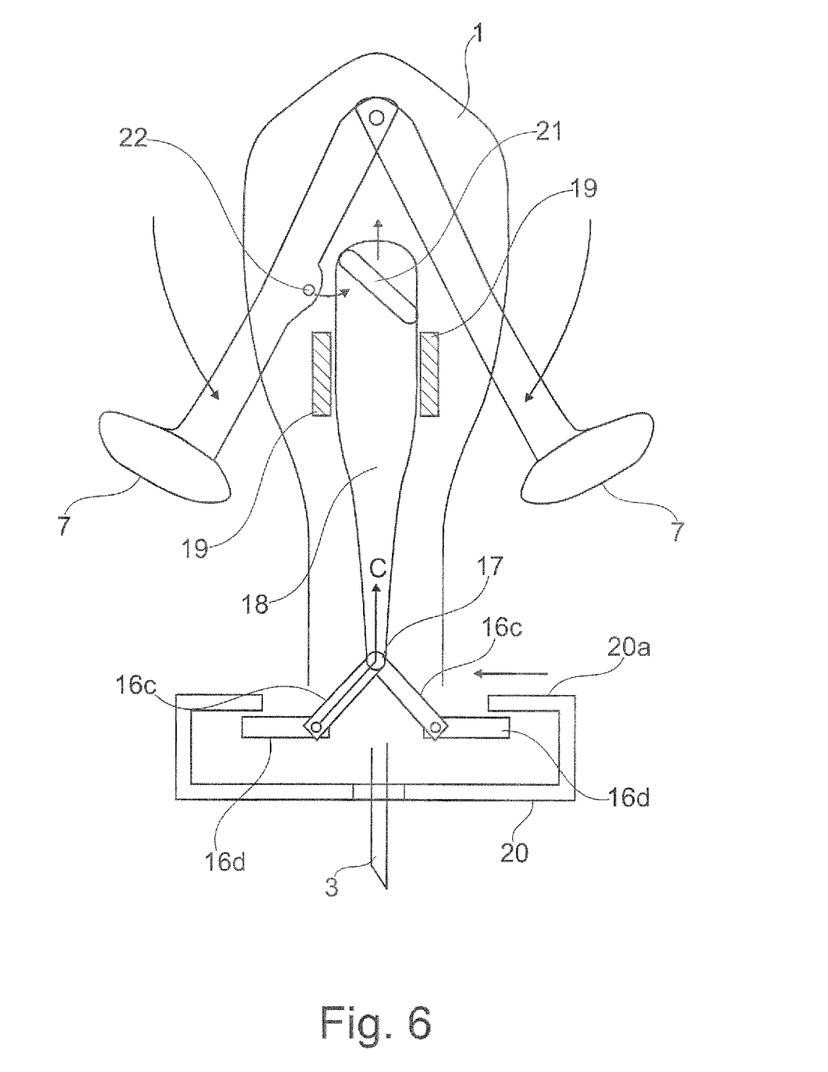
FIG. 6 shows a schematic depiction of a further embodiment of the coupling of an insertion device to a sensor holder.

FIG. 6 shows a schematic illustration of a variation of the embodiment depicted in FIG. 5. Instead of a sinusoidal link mechanism, the two arms 16 are pulled back by an arm 18 that can move between two linear guides 19. Arm 18 includes a slot link 21 which is moved along by a pivot bolt 22 at the end of an actuating motion. In the embodiment shown, pivot bolt 22 is fastened to one of the two actuating elements 7 and impacts a slanted surface of slot link 21 at the end of an actuating motion. This causes arm 18 to move in the direction of arrow C, thereby decoupling the insertion device from sensor holder 20.

Figure 7:
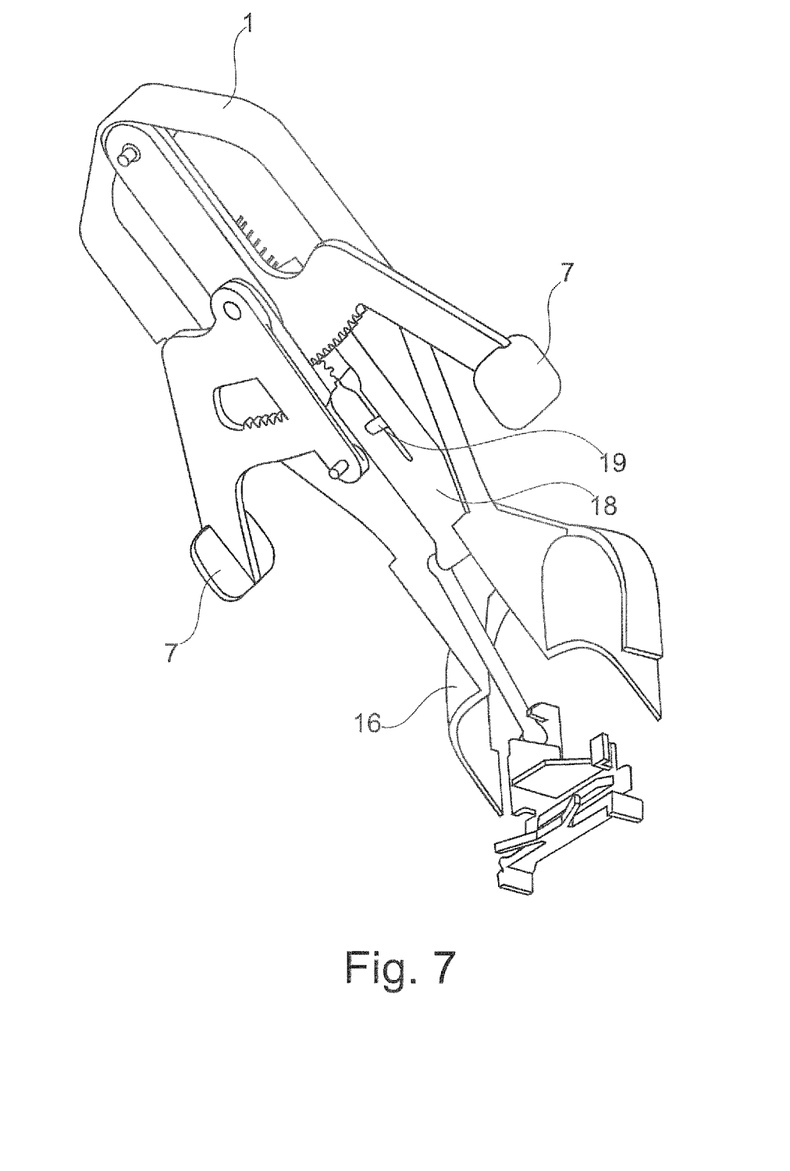
FIG. 7 shows a schematic depiction of a further embodiment of the coupling of an insertion device to a sensor holder.

FIG. 7 shows a further embodiment which is a modification of above-mentioned coupling mechanism 15 explained with reference to FIG. 6. In the case of coupling mechanism 15 depicted in FIG. 7, linear guide 19 is designed as a segment attached to housing 1, which engages in a slot in arm 18. A single arm 16 is hingedly installed on arm 18 and comprises a locking bar which engages, for insertion, into holding elements 20a of sensor holder 20, and, at the end of an insertion procedure, is withdrawn from the engaged position by arm 18, thereby disengaging sensor holder 20 from insertion device 1.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

REFERENCE NUMERALS

1 Housing
2 Insertion needle holder
3 Insertion needle
4 Connecting rod
5 Crank
6 Rotor
7 Actuating element
8 Rack
9 Linear guide
10 Housing underside
11 Rocker pivot
12 Filament
13 Connecting element
15 Coupling mechanism
16 Arm
16a Upper end of the arm
16b Lower end of the arm
16c Upper arm
16d Lower arm
17 Connecting point
18 Arm
19 Linear guide
20 Sensor holder
20a Holding element
21 Slot link
22 Pivot bolt

What is claimed is:
1. An insertion device comprising:
an insertion needle holder,
a drive mechanism for linearly moving the insertion needle holder in a puncturing direction, and
at least one actuating element for actuating the drive mechanism, wherein a non-linear motion of the drive mechanism converts a driving motion of the at least one actuating element, which extends transversely or opposite to the puncturing direction, into a linear puncturing motion of the insertion needle holder by transferring a force applied to the at least one actuating element to the insertion needle holder;
wherein the drive mechanism converts a driving motion of the at least one actuating element, which extends transversely to the puncturing direction, into a punc- turing motion and, immediately thereafter, into retraction motion of the insertion needle holder without reversing the direction of the driving motion; and wherein the puncturing motion occurs during the driving motion.

2. The insertion device according to claim 1, wherein the drive mechanism comprises a connecting rod.

3. The insertion device according to claim 1, wherein the drive mechanism includes a rotor and a connecting rod coupled to the rotor, which converts rotary motion of the rotor into linear motion of the insertion needle holder.

4. The insertion device according to claim 3, wherein the drive mechanism converts the driving motion of the actuating element into rotary motion of the rotor.

5. The insertion device according to claim 4, wherein the drive motion of the at least one actuating element is a swivelling motion.

6. The insertion device according to claim 1, wherein the at least one actuating element includes a rack.

7. The insertion device according to claim 1, wherein the drive mechanism is disposed in a housing, out of which the at least one actuating element extends.

8. The insertion device according to claim 1, further comprising a linear guide for the insertion needle holder.

9. An insertion device comprising:
an insertion needle holder,
a drive mechanism for linearly moving the insertion needle holder in a puncturing direction, and
at least one actuating element for actuating the drive mechanism, wherein a non-linear motion of the drive mechanism converts a driving motion of the at least one actuating element, which extends transversely or opposite to the puncturing direction, into a linear puncturing motion of the insertion needle holder by transferring a force applied to the at least one actuating element to the insertion needle holder:
wherein the drive mechanism converts a driving motion of the at least one actuating element, which extends transversely to the puncturing direction, into a puncturing motion and, immediately thereafter, into retraction motion of the insertion needle holder without reversing the direction of the driving motion; and
wherein the insertion device does not include an energy accumulator which contributes a force to drive the puncturing motion of the insertion needle holder.

10. An insertion device comprising:
an insertion needle holder,
a drive mechanism for linearly moving the insertion needle holder in a puncturing direction, and
at least one actuating element for actuating the drive mechanism, wherein a non-linear motion of the drive mechanism converts a driving motion of the at least one actuating element, which extends transversely or opposite to the puncturing direction, into a linear puncturing motion of the insertion needle holder by transferring a force applied to the at least one actuating element to the insertion needle holder;
wherein the drive mechanism converts a driving motion of the at least one actuating element, which extends transversely to the puncturing direction, into a puncturing motion and, immediately thereafter, into retraction motion of the insertion needle holder without reversing the direction of the driving motion; and
wherein the at least one actuating element comprises two actuating elements which are diametrically opposed.

11. The insertion device according to claim 10, wherein the two actuating elements move in the opposite direction when a puncturing motion occurs.

12. The insertion device according to claim 10, wherein the two actuating elements move toward one another when a puncturing motion occurs.

13. An insertion system comprising:
an insertion device including:
an insertion needle holder;
a drive mechanism for linearly moving the insertion needle holder in a puncturing direction;
at least one actuating element for actuating the drive mechanism, wherein a non-linear motion of the drive mechanism converts a driving motion of the at least one actuating element, which extends transversely or opposite to the puncturing direction, into a linear puncturing motion of the insertion needle holder by transferring a force applied to the at least one actuating element to the insertion needle holder;
a sensor holder, wherein the insertion device comprises a coupling mechanism that, for insertion, holds the sensor holder against the insertion device and is actuated by the drive mechanism at the end of an insertion procedure to detach the sensor holder from the insertion device; and
wherein the coupling mechanism includes a lever arm which is engaged with the sensor holder during the linear insertion motion of the insertion needle holder and wherein actuation of the coupling mechanism by the drive mechanism at the end of the insertion procedure disengages the lever arm from the sensor holder to thereby detach the sensor holder from form the insertion device.

14. The insertion system of claim 13 wherein the lever arm of the coupling mechanism has a pivotal connection.

* * * * *

UNITED STATES PATENT AND TRADEMARK OFFICE
CERTIFICATE OF CORRECTION

PATENT NO. : 10,537,357 B2
APPLICATION NO. : 15/434412
DATED : January 21, 2020
INVENTOR(S) : Frank Deck et al.

Page 1 of 1

It is certified that error appears in the above-identified patent and that said Letters Patent is hereby corrected as shown below:

In the Claims

Column 9, Line 35, Claim 9, the phrase "the insertion needle holder:" should read --the insertion needle holder;--.

Column 10, Line 47, Claim 13, the phrase "detach the sensor holder from form the" should read --detach the sensor holder from the--.

Signed and Sealed this
Tenth Day of March, 2020

Andrei Iancu
*Director of the United States Patent and Trademark Office*